United States Patent
Demirjian

(10) Patent No.: US 10,281,455 B2
(45) Date of Patent: May 7, 2019

(54) PREDICTION OF ACUTE KIDNEY INJURY FROM A POST-SURGICAL METABOLIC BLOOD PANEL

(71) Applicant: THE CLEVELAND CLINIC FOUNDATION, Cleveland, OH (US)

(72) Inventor: Sevag G. Demirjian, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 126 days.

(21) Appl. No.: 15/262,556

(22) Filed: Sep. 12, 2016

(65) Prior Publication Data

US 2016/0377595 A1 Dec. 29, 2016

Related U.S. Application Data

(62) Division of application No. 13/911,236, filed on Jun. 6, 2013.

(Continued)

(51) Int. Cl.
*G01N 33/49* (2006.01)
*G06F 19/00* (2018.01)
(Continued)

(52) U.S. Cl.
CPC ............ *G01N 33/492* (2013.01); *G01N 33/62* (2013.01); *G01N 33/70* (2013.01); *G01N 33/84* (2013.01); *G06F 19/00* (2013.01); *G16H 50/20* (2018.01); *G16H 50/50* (2018.01); *G01N 2333/765* (2013.01); *G01N 2800/347* (2013.01); *G01N 2800/52* (2013.01); *Y10T 436/147777* (2015.01)

(58) Field of Classification Search
CPC ............................ G16H 50/50; G01N 33/492
See application file for complete search history.

(56) References Cited

U.S. PATENT DOCUMENTS

| | | | |
|---|---|---|---|
| 2010/0183520 A1* | 7/2010 | Ramesh | C12Q 1/6883 424/9.2 |
| 2011/0055141 A1* | 3/2011 | Jamil | G06K 9/6234 706/54 |
| 2012/0077690 A1* | 3/2012 | Singbartl | G01N 33/6893 506/9 |

FOREIGN PATENT DOCUMENTS

| WO | 2011143232 A1 | 11/2011 |
|---|---|---|
| WO | 2011162820 A1 | 12/2011 |

OTHER PUBLICATIONS

Predictive Models for Acute Kidney Injury Following Cardiac Surgery Sevag Demirjian, Jesse D. Schold, Jose Navia, Tara M. Mastracci, Emil P. Paganini, Jean-Pierre Yared, and Charles A. Bashour Am J Kidney Dis. 59(3): 382-389 (Year: 2012).*

(Continued)

*Primary Examiner* — Krishnan S Menon
*Assistant Examiner* — Dwan A Gerido
(74) *Attorney, Agent, or Firm* — Tarolli, Sundheim, Covell & Tummino LLP

(57) ABSTRACT

Systems and methods are provided for predicting the likelihood of acute kidney injury. An input interface is configured to receive a plurality of features derived from the results of a post-surgical metabolic blood panel and either a pre-surgical metabolic blood panel or a perisurgical metabolic blood panel. A predictive model is configured to calculate a parameter representing a likelihood of acute kidney injury from the plurality of features. A user interface is configured to provide the calculated parameter to a user in a human comprehensible form.

9 Claims, 2 Drawing Sheets

Related U.S. Application Data

(60) Provisional application No. 61/656,258, filed on Jun. 6, 2012.

(51) Int. Cl.
    *G01N 33/62*    (2006.01)
    *G01N 33/70*    (2006.01)
    *G01N 33/84*    (2006.01)
    *G16H 50/50*    (2018.01)
    *G16H 50/20*    (2018.01)

(56) References Cited

OTHER PUBLICATIONS

Serum Cystatin C in Elderly Cardiac Surgery Patients Anne Ristikankare, Reino Poyhia, Anne Kuitunen, Markus Skrifvars, Pekka Hammainen, Markku Salmenpera, Raili Suojaranta-Ylinen Ann Thorac Surg 2010;89:689-695 (Year: 2010).*

Wellwood et al., "Urinary N-Acetyl-13-D-Glucosarninidase Activities in Patients with Renal Disease", British Medical Journal, 1975, pp. 408-411.

Han et al., "Kidney Injury Molecule-1 (KIM-1): A Novel Biomarker for Human Renal Proximal Tubule Injury", Kidney International, 2002, vol. 62, pp. 237-244.

Mishra et al., "Identification of Neutrophil Gelatinase-Associated Lipocalin as a Novel Early Urinary Biomarker for Ischemic Renal Injury", Journal of the American Society of Nephrology, 2003, vol. 14, pp. 2534-2543.

Herget-Rosenthal et al., "Early Detection of Acute Renal Failure by Serum Cystatin C", Kidney International, 2004, vol. 66, pp. 1115-1122.

Parikh, MD, PhD et al., "Urinary Interleukin-18 is a Marker of Human Acute Tubular Necrosis", American Journal of Kidney Diseases, 2004, vol. 43, No. 3, pp. 405-414.

Lassnigg et al., "Minimal Changes of Serum Creatinine Predict Prognosis in Patients after Cardiothoracic Surgery: A Prospective Cohort Study", Journal of the American Society of Nephrology, 2004, vol. 15, pp. 1597-1605.

Thakar et al., "A Ciinical Score to Predict Acute Renal Failure after Cardiac Surgery", Journal of the American Society of Nephrology, 2005, vol. 16, 162-168.

Wijeysundera MD et al., "Derivation and Validation of a Simplified Predictive Index for Renal Replacement Therapy After Cardiac Surgery", American Medical Association, 2007, vol. 297, No. 16, pp. 1801-1809.

Ristikankare MD et al., "Serum Cystatin C in Elderly Cardiac Surgery Patients", The Society of Thoracic Surgeons, 2009, pp. 689-694.

Bagshaw MD et al., "Timing of Renal Replacement Therapy and Clinical Outcomes in Critically Ill Patients with Severe Acute Kidney Injury", Journal of Critical Care, 2009, vol. 24, pp. 129-140.

Demirjian MD et al., "Predictive Models for Acute Kdiney Injury Following Cardiac Surgery", American Journal of Kidney Disorder, 2012, vol. 59, pp. 382-389.

PCT International Search Report and Written Opinion, dated Aug. 16, 2013, pp. 1-10

* cited by examiner

PREDICTION OF ACUTE KIDNEY INJURY FROM A POST-SURGICAL METABOLIC BLOOD PANEL

RELATED APPLICATION

This application claims priority to and is a divisional application of currently U.S. application Ser. No. 13/911,236, filed Jun. 6, 2013, published as U.S. Publication No. US-2015-0055093-A1 on Feb. 26, 2015, which in turns claims priority to U.S. Provisional Patent Application Ser. No. 61/656,258, filed Jun. 6, 2012. The entirety of each of these applications is hereby incorporated by reference for all purposes.

FIELD OF THE INVENTION

The present invention relates to systems and methods for diagnosing illness in a living being and, in particular, is directed to systems and methods for predicting the occurrence of acute kidney injury from parameters derived from a post-surgical metabolic blood panel.

BACKGROUND OF THE INVENTION

Acute kidney injury (AKI) is a rapid loss of kidney function, which in its severe form, is associated with significant morbidity and mortality. Its causes are numerous and include low blood volume from any cause, exposure to substances harmful to the kidney, and obstruction of the urinary tract. As a result, AKI can be a complication from a surgical procedure, particular cardiac surgery. AKI may lead to a number of complications, including metabolic acidosis, high potassium levels, uremia, changes in body fluid balance, and effects to other organ systems. Management includes supportive care, such as renal replacement therapy, as well as treatment of the underlying disorder, and the effectiveness of treatment of AKI increases greatly with timely diagnosis.

SUMMARY OF THE INVENTION

In accordance with an aspect of the present invention, a non-transitory computer readable medium stores machine executable instructions for predicting the likelihood of acute kidney injury. An input interface is configured to receive a plurality of features derived from the results of a post-surgical metabolic blood panel and either a pre-surgical metabolic blood panel or a perisurgical metabolic blood panel. A predictive model is configured to calculate a parameter representing a likelihood of acute kidney injury from the plurality of features. A user interface is configured to provide the calculated parameter to a user in a human comprehensible form.

In accordance with another aspect of the present invention, a method is provided for predicting acute kidney injury from a surgical procedure. A first blood serum sample is isolated from a blood sample drawn from a patient before an end of the surgical procedure. A first creatinine level is determined from the first blood serum sample. A second blood serum sample is isolated from a blood sample drawn from the patient after the end of the surgical procedure. A second creatinine level is determined from the second blood serum sample. From a predictive model, a parameter is calculated representing a likelihood of acute kidney injury to the patient from at least the difference between the first creatinine level and the second creatinine level. The calculated parameter is displayed to a user.

In accordance with still another aspect of the present invention, a diagnostic system includes a processor and a non-transitory computer readable medium storing machine executable instructions executable by the processor to predict a likelihood of acute kidney injury. The instructions include an input interface configured to receive a plurality of features derived from the results of a post-surgical metabolic blood panel and either a pre-surgical metabolic blood panel or a perisurgical metabolic blood panel. The plurality of features include a difference in a serum creatinine level between the pre-surgical metabolic blood panel or the perisurgical metabolic blood panel and the post-surgical metabolic blood panel. A predictive model is configured to calculate a parameter representing a likelihood of acute kidney injury from the plurality of features. A user interface configured to provide the calculated parameter to a user in a human comprehensible form.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
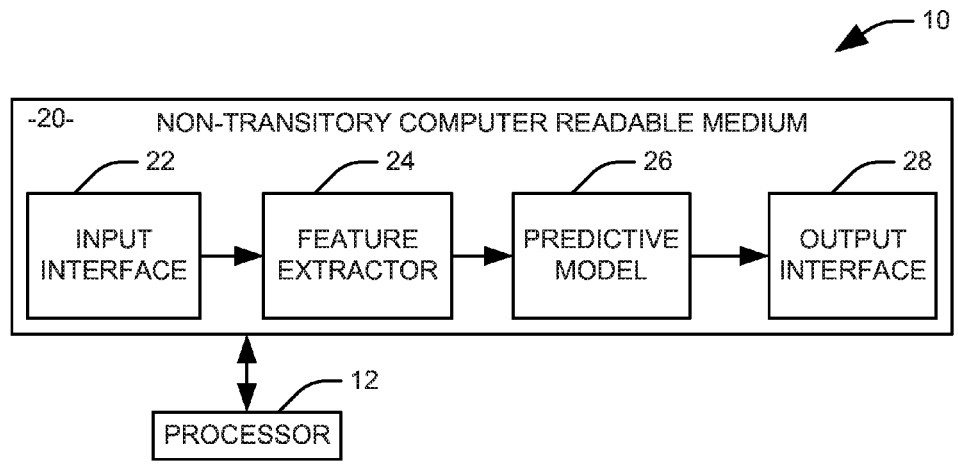
FIG. 1 illustrates a system for predicting acute kidney injury with parameters derived from a post-surgical metabolic blood panel in accordance with an aspect of the present invention.

FIG. 1 illustrates a system 10 for predicting the likelihood of acute kidney injury in accordance with an aspect of the present invention. Specifically, the illustrated system 10 utilizes parameters derived from a standard post-surgical metabolic blood panel to accurately predict the likelihood of an acute kidney injury, defined for the purposes of this application as a rapid loss of kidney function resulting in a need for treatment via dialysis. It will be appreciated that the illustrated system 10 can be implemented as dedicated hardware, software instructions stored on one or more computer readable media, or a combination of hardware and software. In the illustrated system 10, a software implementation is used, with a general purpose processor 12 executing machine readable instructions stored on a non-transitory computer readable medium 20.

The instructions can include an input interface 22 configured to receive a plurality of features derived from the results of a post-surgical metabolic blood panel. For example, the input interface 22 can comprise machine readable instructions for providing an input screen to a user to allow the user to enter the plurality of features via an appropriate input device (not shown), such as a keyboard, mouse, or microphone. In an alternative implementation, the input interface 22 is configured to interact with a medical database or other automated data source to extract the plurality of features from recorded results of one or more post-surgical metabolic blood panels.

In accordance with an aspect of the present invention, the plurality of features comprise various parameters derived from the determined concentrations of various substances of interest within a patient's blood following surgery. These parameters are calculated from the received post-surgical metabolic blood panel data at a feature extractor 24. For example, the substances of interest can include two or more of serum creatinine, blood urea nitrogen, potassium, sodium, bicarbonate, and albumin. The derived parameters can include, for example, the concentrations themselves, a rate of change of a given concentration since the surgery, exponential powers of the concentrations or associated rates of change, and products of concentrations and/or rates of change. For example, the derived parameters can include the concentrations of potassium, sodium, bicarbonate, and albumin, the rate of change (per hour) of serum creatinine and blood urea nitrogen, and one or more cubic terms derived from each of the rate of change of the serum creatinine and the concentrations of sodium and bicarbonate.

The parameters derived for the plurality of features are provided to a predictive model 26, which is configured to calculate a parameter representing a likelihood of acute kidney injury from the plurality of features. It will be appreciated that the predictive model 26 can be implemented as any appropriate classification or regression model, such as a polynomial model provided via least squares regression procedure, an artificial neural network, a statistical classifier, a support vector machine, or other, similar model. In the illustrated implementation, each of the plurality of features has an associated weight, and the predictive model 26 provides a linear combination of the plurality of features. It will be appreciated, however, that since the features themselves can be non-linear functions of the measured concentrations and rates of change, the results of the predictive model can be a non-linear function of the measured concentrations and rates of change. The output of the predictive model 26 represents the likelihood of an acute kidney injury requiring dialysis. An output interface 28 is configured to provide the calculated parameter to a user in a human comprehensible form. Specifically, the output interface 28 interacts with a display, printer, speaker, or other appropriate output device (not shown) to provide the calculated likelihood of acute kidney injury to a user.

Acute kidney injury is a serious complication of surgery, and its severe form is associated with significant morbidity and mortality. Serum creatinine and blood urea in conjunction with urine output have been the traditional means of diagnosis, and management, however clinically notable changes often take days to appear after injury, and hence preclude early therapeutic interventions. New biomarkers such as IL-18 and urine neutrophil gelatinase-associated lipocalin (NGAL) are among many others which have been studied subjects undergoing cardiac surgery; however risk prediction markers, reflected by the area under the receiver-operating characteristic curve (AUC) have been mediocre at best. Moreover, due to the low incidence of severe AKI requiring dialysis, most predictive models were evaluated using creatinine change as the main or predominant endpoint, or dependent variable, as opposed to provision of renal replacement therapy.

Using the readily available and frequently tested early postoperative basic metabolic panel, the inventors have developed a highly discriminative predictive model for AKI requiring dialysis following cardiac surgery. The extended model included preoperative serum creatinine, change in creatinine, and BUN from preoperative values, and serum sodium, potassium, bicarbonate, and albumin. Serum creatinine is a poor marker of the glomerular filtration rate early in AKI due to the lag period required for it to reach steady state (i.e., a constant generation rate). The more severe and abrupt the decline in renal function the larger the discrepancy. In the system of FIG. 1, this is remedied by using the rate of change in serum creatinine over time, rather than the absolute value. In the current study, even within a twenty-four hour window, the rate of change outperformed the absolute change serum creatinine. Moreover, the inclusion of other elements in the panel as potassium, sodium, and bicarbonate also independently contributed to the predictive capacity of the model because they capture clinically relevant downstream complications of renal injury in a multi-dimensional approach, such as electrolyte perturbations and acid acid-base derangements. Whereas, serum albumin adjusts for volume shifts that typically occur during surgery, which account not only for the burden but also influence the rate and magnitude of change of elements in metabolic panel.

Figure 2:
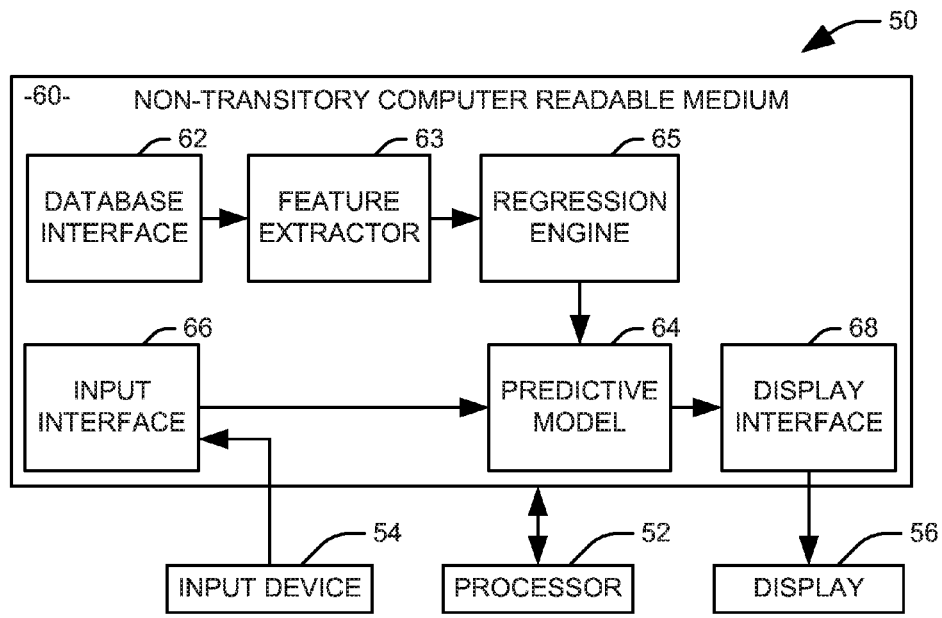
FIG. 2 illustrates one example of a system for predicting acute kidney injury in accordance with an aspect of the present invention.

FIG. 2 illustrates one example of a system 50 for predicting acute kidney injury in accordance with an aspect of the present invention. Specifically, the system 50 uses laboratory data from a first postoperative metabolic panel to calculate a change in serum creatinine ($\Delta Cr$) and blood urea nitrogen ($\Delta BUN$) compared to values from a preoperative or perioperative metabolic blood panel. Each of $\Delta Cr$, and $\Delta BUN$ can be normalized by the time interval from surgery to the first laboratory draw. The system can also utilize serum potassium, bicarbonate, sodium, and albumin levels from the same metabolic panel to further refine the results. The predictor variables were limited to those available in routine metabolic panel which is frequently checked in the perioperative period. The illustrated system 50 can be implemented as a networked computer, comprising a processor 52, input device 54, display 56, and a non-transitory computer readable medium 60. In one implementation, the system 50 can be implemented as an online calculator accessed via a remote computer via the Internet. In such a system, it will be appreciated that the input device 54 and display 56 are located remotely from the non-transitory medium 60.

During a training process, records can be retrieved from an electronic health records (EHR) database via a database interface 62, and predictor variables and the outcomes can be extracted from these records at an associated feature extractor 63. One or more predictive models 64 can be generated at a regression engine 65 using features from these metabolic panels and the provision of dialysis within two weeks of surgery (or discharge/death if sooner), as a primary outcome measure. In the illustrated implementation, a least squares regression is performed using restricted cubic splines with either four knot locations, at the fifth, thirty-fifth, sixty-fifth, and ninety-fifth percentiles, or five knot locations, at the fifth, twenty-seven and five-tenths, fiftieth, seventy-two and five-tenths, and ninety-fifth percentiles to allow for flexible nonlinear associations with the primary outcome measure using logistic regression. The training set can be limited to fifteen events per predictor degree of freedom, inclusive of the degrees spent due to use of cubic splines, to avoid overfitting the model. In this implementation, the result of each model can be represented as a plurality of sets of at least three parameters for each feature, with a linear term and plurality of parameters representing the non-linear (e.g., cubic) terms of the fitted curve.

One example of a predictive model uses a difference between the pre/perioperative serum creatinine as the sole feature. In another example, this difference is normalized according to a length of time between the end of the surgery and the performance of the postsurgical metabolic panel, for example, as a number of hours. Using the normalized value allows for the rate of change of the creatinine to be measured, which the inventor has determined to be a better predictor of the decline in renal function. In a third model, the normalized change in serum creatinine can be used along with the preoperative serum creatinine to further refine the model.

For a fourth model, readily available and frequently tested early postoperative basic metabolic panel parameters can be used to provide an extended model. Specifically, the extended model includes preoperative serum creatinine, the normalized change in creatinine and BUN from preoperative values, and serum sodium, potassium, bicarbonate, and albumin. The inclusion of the additional elements in the panel such as potassium, sodium, and bicarbonate also independently contribute to the predictive capacity of the model because they capture clinically relevant downstream complications of renal injury in a multidimensional approach, such as electrolyte perturbations, and acid-base derangements. Serum albumin adjusts for volume shifts that typically occur during surgery, which account not only for the volume burden but also influence the rate and magnitude of change of all elements in the metabolic panel. Table 1 provides example values for each of these four models as determined by the inventor.

TABLE 1

|  | $\Delta$Cr | $\Delta$Cr/hour$^a$ | Prosperative Cr | $\Delta$BUN/hour$^a$ |
|---|---|---|---|---|
| Model 1 | | | | |
| Linear term | −5.03 (<.001) | | | |
| $1^{st}$ cubic term | 38.42 (<.001) | | | |
| $2^{nd}$ cubic term | −138.03 (<.001) | | | |
| P, linear$^b$ | <.001 | | | |
| P, nonlinear$^c$ | <.001 | | | |
| Model 2 | | | | |
| Linear term | | −16.61 (<.001) | | |
| $1^{st}$ cubic term | | −198.86 (.007) | | |
| $2^{nd}$ cubic term | | 2486.9 (<.001) | | |
| $3^{rd}$ cubic term | | −7563.4 (<.001) | | |
| P, linear$^b$ | | <.001 | | |
| P, nonlinear$^c$ | | <.001 | | |
| Model 3 | | | | |
| Linear term | | −9.94 (<.001) | −1.56 (.11) | |
| $1^{st}$ cubic term | | −33.5 (.65) | 24.41 (<.001) | |
| $2^{nd}$ cubic term | | 1261.8 (.006) | −55.20 (<.001) | |
| $3^{rd}$ cubic term | | −4527.0 (<.001) | | |
| P, linear$^b$ | | <.001 | <.001 | |
| P, nonlinear$^c$ | | <.001 | <.001 | |
| Model 4 | | | | |
| Linear term | | −1.31 (.10) | −0.79 (.45) | −0.318 (.001) |
| $1^{st}$ cubic term | | 52.09 (.50) | 19.22 (.003) | −1.006 (.37) |
| $2^{nd}$ cubic term | | 649.12 (.17) | −43.84 (.002) | 12.374 (.46) |
| $3^{rd}$ cubic term | | −3077.35 (.005) | | −22.213 (.56) |
| P, linear$^b$ | | <.001 | <.001 | <.001 |
| P, nonlinear$^c$ | | <.001 | .003 | .07 |

|  | Sodium | Potassium | Bicarbonate | Aluminum | C statistic |
|---|---|---|---|---|---|
| Model 1 | | | | | |
| Linear term | | | | | 0.768 |
| $1^{st}$ cubic term | | | | | |
| $2^{nd}$ cubic term | | | | | |
| P, linear$^b$ | | | | | |
| P, nonlinear$^c$ | | | | | |
| Model 2 | | | | | |
| Linear term | | | | | 0.779 |
| $1^{st}$ cubic term | | | | | |
| $2^{nd}$ cubic term | | | | | |
| $3^{rd}$ cubic term | | | | | |
| P, linear$^b$ | | | | | |
| P, nonlinear$^c$ | | | | | |
| Model 3 | | | | | |
| Linear term | | | | | 0.866 |
| $1^{st}$ cubic term | | | | | |
| $2^{nd}$ cubic term | | | | | |
| $3^{rd}$ cubic term | | | | | |
| P, linear$^b$ | | | | | |
| P, nonlinear$^c$ | | | | | |

TABLE 1-continued

Model 4

| | | | | | |
|---|---|---|---|---|---|
| Linear term | −0.129 (<.001) | −0.728 (.03) | −0.1243 (<.001) | −1.344 (<.001) | 0.899 |
| 1$^{st}$ cubic term | 0.267 (0.03) | 1.170 (.48) | 0.0761 (.51) | 1.007 (.22) | |
| 2$^{nd}$ cubic term | −0.601 (.32) | −2.121 (.68) | 0.2344 (.72) | −3.948 (.49) | |
| 3$^{rd}$ cubic term | | | | | |
| P, linear$^b$ | <.001 | .02 | <.001 | <.001 | |
| P, nonlinear$^c$ | <.001 | .10 | <.001 | .16 | |

During operation, a user can use the input device 54 to provide values for the features via an input interface 66. These values are then provided to the predictive model 64 which calculates a parameter representing the likelihood of acute kidney injury requiring dialysis as a weighted non-linear combination of the plurality of features based upon the set of linear and non-linear weights associated with each feature. The resulting parameter can be provided to a display via a display interface 68 to inform the user of the likelihood that a patient represented by the features will require dialysis.

Figure 3:
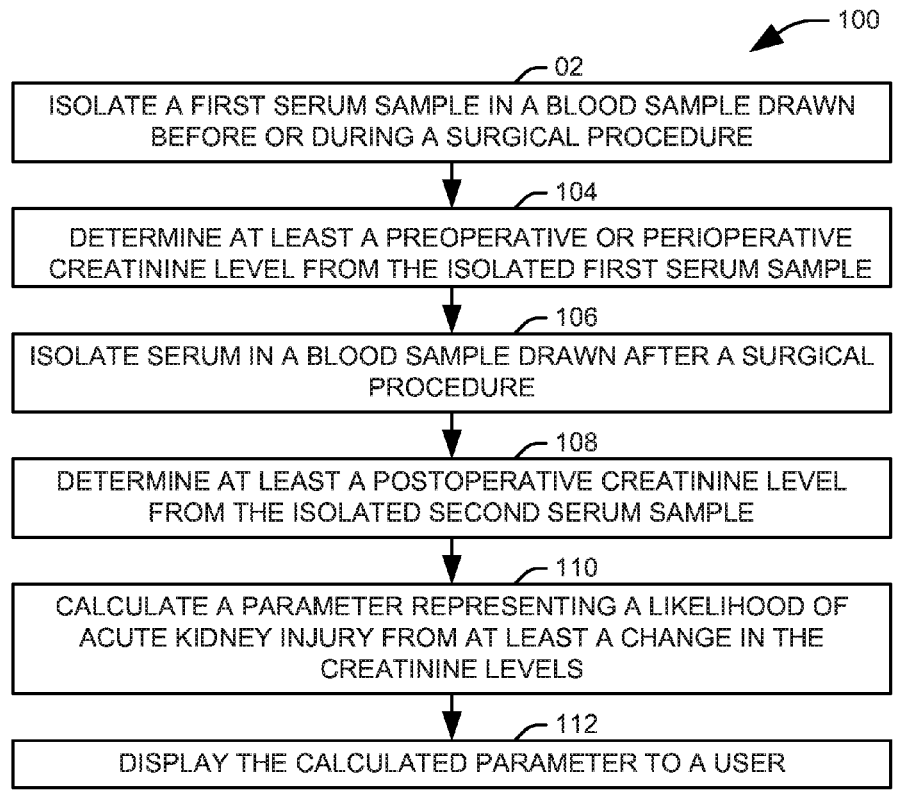
FIG. 3 illustrates a method for predicting acute kidney injury (AKI) in accordance with an aspect of the present invention.

It will be appreciated that the models 64 are based solely on routine metabolic panel that can be obtained within hours of surgery, allowing for early diagnosis of acute kidney injury. The extended model also incorporates the time lapse from the injury event to the laboratory draw, without posing any time restrictions. The use of readily available, standardized, and affordable predictors from routine metabolic panel makes the predictive model easily applicable to any patient. While the example given in Table 1 represents patients undergoing cardiac surgery, the model could easily be extended, with appropriate validation, to virtually any non-cardiac setting. Finally, the model has is sufficiently sophisticated to capture complex non-linear relationships between the parameters associated with the routine metabolic blood panel and FIG. 3 illustrates a method 100 for predicting acute kidney injury (AKI) in accordance with an aspect of the present invention. Specifically, the method uses changes in basic metabolic panel early after surgery to predict severe AKI requiring dialysis within a two week period following surgery. At 102, blood drawn for a preoperative or perioperative metabolic blood panel is mechanically separated to isolate a first serum sample. For example, a blood sample can be drawn from the patient and spun in a centrifuge to separate out blood serum. At 104, a preoperative or perioperative level of serum creatinine is determined from the first blood serum sample. It will be appreciated, however, that other parameters can be extracted from the preoperative or perioperative metabolic blood panel, for example, a blood urea nitrogen level.

At 106, blood drawn for a post-operative metabolic blood panel is mechanically separated to isolate a second serum sample. At 108, a post-operative level of serum creatinine is determined from the second blood serum sample. It will be appreciated, however, that other parameters can be extracted from the preoperative or perioperative metabolic blood panel, for example, levels for blood urea nitrogen, sodium, potassium, bicarbonate, and albumin. At 110, a parameter representing a likelihood of acute kidney injury to the patient is calculated from at least a difference between the preoperative or perioperative creatinine level and the post-operative creatinine level. In one implementation, this difference can be normalized according to the length of a period of time (e.g., in hours) between the end of the surgical procedure and the drawing of the post-operative metabolic blood panel. It will be appreciated that other features can be used to refine the calculation including any or all the sodium level, potassium level, bicarbonate level, and albumin level determined from the post-operative blood serum sample, the creatinine level from the first serum sample, and a difference between the blood urea nitrogen level from the first serum sample and the blood urea nitrogen level from the second serum sample normalized by the period of time between the end of the surgical procedure and the drawing of the post-operative metabolic blood panel. At 112, the calculated parameter is provided to a user at an associated display. If the parameter is within a range associated with a severe risk of acute kidney injury, the user can begin appropriate treatment.

Figure 4:
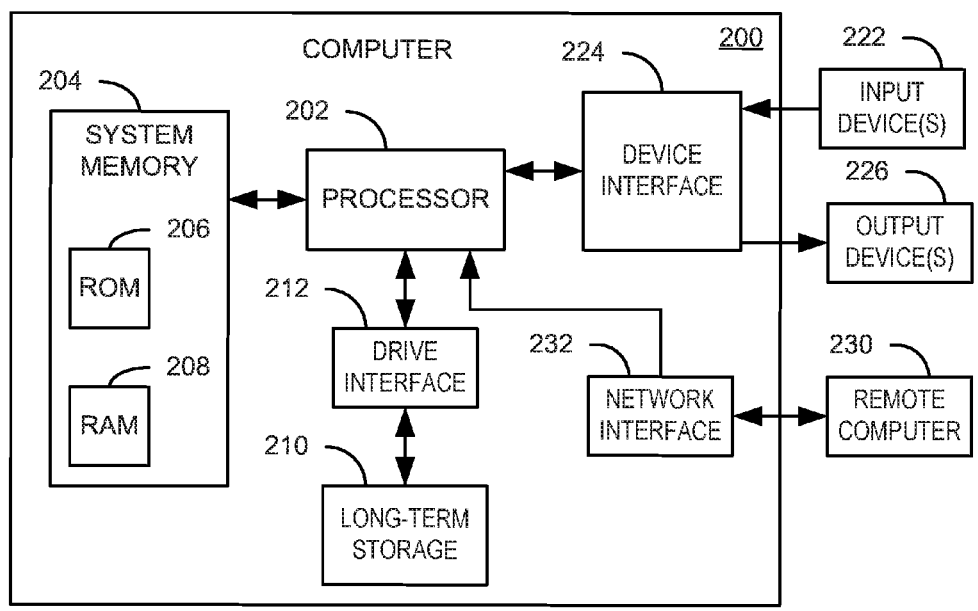
FIG. 4 illustrates a computer system that can be employed to implement systems and methods described herein.

FIG. 4 illustrates a computer system 200 that can be employed to implement systems and methods described herein, such as based on computer executable instructions running on the computer system. The user may be permitted to preoperatively simulate the planned surgical procedure using the computer system 200 as desired. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 206 and random access memory (RAM) 208. A basic input/output system (BIOS) can reside in the ROM 206, generally containing the basic routines that help to transfer information between elements within the computer system 200, such as a reset or power-up.

The computer system 200 can include one or more types of long-term data storage 210, including a hard disk drive, a magnetic disk drive, (e.g., to read from or write to a removable disk), and an optical disk drive, (e.g., for reading a CD-ROM or DVD disk or to read from or write to other optical media). The long-term data storage 210 can be connected to the processor 202 by a drive interface 212. The long-term data storage 210 components provide nonvolatile storage of data, data structures, and computer-executable instructions for the computer system 200. A number of program modules may be stored in one or more of the drives as well as in the RAM 208, including an operating system, one or more application programs, other program modules, and program data.

A user may enter commands and information into the computer system 200 through one or more input devices 222, such as a keyboard or a pointing device (e.g., a mouse). These and other input devices are often connected to the processor 202 through a device interface 224. For example, the input devices can be connected to the system bus by one or more a parallel port, a serial port or a universal serial bus (USB). One or more output device(s) 226, such as a visual display device or printer, can also be connected to the processor 202 via the device interface 224.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for predicting the likelihood of acute kidney injury comprising:
   receiving a plurality of features derived from the results of a post-surgical metabolic blood panel and one of a pre-surgical metabolic blood panel and a perisurgical metabolic blood panel at an input interface associated with a predictive model;
   calculating a parameter representing a likelihood of acute kidney injury from the plurality of features via the predictive model, each of the input interface and the predictive model being implemented as machine executable instructions stored on a non-transitory computer readable medium and the plurality of features including a difference in a creatinine level between the one of the pre-surgical metabolic blood panel and the perisurgical metabolic blood panel and the post-surgical blood panel divided by a time elapsed between a surgery and the post-surgical metabolic blood panel; and
   providing dialysis to the patient if the calculated parameter is within a range associated with a severe risk of acute kidney injury.

2. The method of claim 1, wherein the plurality of features includes a sodium level from the post-surgical metabolic blood panel.

3. The method of claim 1, wherein the plurality of features includes a potassium level from the post-surgical metabolic blood panel.

4. The method of claim 1, wherein the plurality of features includes a bicarbonate level from the post-surgical metabolic blood panel.

5. The method of claim 1, wherein the plurality of features includes an albumin level from the post-surgical metabolic blood panel.

6. The method of claim 1, wherein the plurality of features includes a difference in a blood urea nitrogen level between the one of the pre-surgical metabolic blood panel and the perisurgical metabolic blood panel and the post-surgical blood panel.

7. The method of claim 6, wherein the difference in the blood urea nitrogen level is divided by a time elapsed between a surgery and the post-surgical metabolic blood panel.

8. A method for predicting the likelihood of acute kidney injury comprising:
   receiving a plurality of features derived from the results of a post-surgical metabolic blood panel and one of a pre-surgical metabolic blood panel and a perisurgical metabolic blood panel at an input interface associated with a predictive model;
   calculating a parameter representing a likelihood of acute kidney injury from the plurality of features via the predictive model, each of the input interface and the predictive model being implemented as machine executable instructions stored on a non-transitory computer readable medium and the plurality of features including a difference in a blood urea nitrogen level between the one of the pre-surgical metabolic blood panel and the perisurgical metabolic blood panel and the post-surgical blood panel divided by a time elapsed between a surgery and the post-surgical metabolic blood panel; and
   providing treatment to the patient if the calculated parameter is within a range associated with a severe risk of acute kidney injury.

9. The method of claim 8, wherein the change in the blood urea nitrogen level is normalized by a time elapsed between a surgery and the post-surgical metabolic blood panel.

* * * * *